United States Patent [19]
Evtodienko et al.

[11] Patent Number: 5,858,797
[45] Date of Patent: Jan. 12, 1999

[54] TEST COMPOSITION, DEVICE AND METHOD FOR THE COLORIMETRIC DETERMINATION OF PHOSPHORUS

[75] Inventors: Yuriy Vladimirovich Evtodienko, Moscow, Russian Federation; Michael Allen Van Lente, Elkhart, Ind.

[73] Assignee: Environmental Test Systems, Inc., Elkhart, Ind.

[21] Appl. No.: 869,820

[22] Filed: Jun. 5, 1997

[51] Int. Cl.⁶ .................................................. G01N 33/00
[52] U.S. Cl. .................. 436/105; 436/103; 436/166; 436/169; 422/50; 422/61
[58] Field of Search ................. 422/56, 61; 436/103, 436/105, 164, 166, 169

[56] References Cited

U.S. PATENT DOCUMENTS

| | | | |
|---|---|---|---|
| 3,785,771 | 1/1974 | Luchsinger et al. | 436/105 X |
| 4,599,316 | 7/1986 | Hahn et al. | 436/105 |
| 4,731,331 | 3/1988 | Shu et al. | 436/105 X |

FOREIGN PATENT DOCUMENTS

| | | |
|---|---|---|
| 261440 | 10/1988 | Germany . |
| 254868 | 10/1969 | U.S.S.R. . |
| 1270697 | 11/1986 | U.S.S.R. . |
| 9325900 | 12/1993 | WIPO . |

OTHER PUBLICATIONS

D.T. Bukns et al. *Anal. Chim. Acta* 1981, 128, 257–260.
M. Namiki *Fresenius Z. Anal. Chem.* 1988, 330, 637–638.
Y. Osawa et al. *Bull. Chem. Soc. Jpn.* 1991, 64, 2648–2655.
C. Matsubara et al. *Analyst* 1993, 118, 553–556.

*Primary Examiner*—Arlen Soderquist
*Attorney, Agent, or Firm*—Zarley, McKee, Thomte, Voorhees & Sease

[57] ABSTRACT

A unitized, one step test reagent composition, device and method is presented for the determination of phosphorus in various test sample fluids such as soil extracts. The invention is a modification of the Murphy and Riley methodology which utilizes a molybdate salt and a reducing agent to generate "molybdenum blue" in the presence of phosphate. In addition to the molybdate salt, the test reagent composition includes a chromogenic reducing agent which contributes to the color development and a solid buffer. The composition is preferably incorporated into a matrix such as paper for ease of handling.

18 Claims, No Drawings

TEST COMPOSITION, DEVICE AND METHOD FOR THE COLORIMETRIC DETERMINATION OF PHOSPHORUS

FIELD OF THE INVENTION

The present invention relates to an improved calorimetric dry reagent test composition, device and method for the determination of phosphorus in various aqueous fluids based on the classic molybdenum blue methodology of Murphy and Riley. Although the improved test system is primarily very useful as a field or on-site test device or kit, it can advantageously be used for multiple sample testing and screening in an analytical chemistry laboratory setting.

BACKGROUND OF THE INVENTION

Since the original introduction by Murphy and Riley of their method for determination of inorganic phosphorus, a great deal of interest in its use for the determination of phosphate in natural waters or body fluids such as blood serum has been expressed by researchers and commercial interests. Indeed, this and closely related methods are the only ones in common use for the colorimetric determination of phosphorus.

The Murphy and Riley method is based on the formation of a complex between phosphate and molybdate which can be quantitated by using its absorption peak in the ultraviolet range or by reducing the complex to produce the blue color of "molybdenum blue" and/or of a series of fairly complex structures known as "heteropoly blues". A significant part of the challenge of this work is to achieve a testing methodology having the necessary convenience of an on-site or field type device coupled with the required sensitivity, rapid rate of reaction and stable color suitable for quantitative work as well as to eliminate positive interferences that can be seen in the presence of silicates, arsenates, or proteins or negative interference from fluoride.

Over the years, researchers have devoted considerable effort to the solution of the above problems and to developing an understanding of the complexity of the chemical structures involved in the presentation of color. "Molybdenum blue" is now understood to have a large structure involving as many as 154 molybdenum atoms, and reaction conditions are thought to determine the combination of "heteropoly blues" that are formed. Because of the complexity of interferences observed, various reactions and associated rates, and incompletely characterized product mixtures, workers have traditionally struggled to achieve reliability and reproducibility in tests based on quantitation of this blue color.

As an exemplary illustration of the application of the present invention, the management of soil chemistry made possible by soil testing is known to farmers to play an important part in the successful production of fruits and vegetables. Farmers typically sample various portions of their fields and send samples to professional laboratories for evaluation of the levels of chemical components including that of soil phosphorus. The Bray method is most commonly used for this and involves extraction of phosphate from the soil using an aqueous sodium bisulfate/sodium fluoride solution followed by reaction of the extract with molybdate and reduction of the resulting complex with ascorbic acid to form a blue color. The visible absorption peak is then used for quantitation in a spectrophotometer. Of course, the same need for testing applies to home gardeners of fruits, vegetables, or flowers, so there is a need for an inexpensive, reliable test method which can be used on site to rapidly obtain a useful result. Soil test kits currently available in this market generally require a cumbersome number of steps and relatively lengthy waiting periods between such steps.

The present invention describes a new way of measuring phosphorus concentration that has accuracy sufficient for the purpose and is faster and more convenient than previously known methods.

DESCRIPTION OF THE PRIOR ART

Patent and literature references relating to methods and compositions for determining phosphorus and phosphates are numerous and go back considerably in time. This presentation of the prior art relating to the present invention will be restricted to calorimetric methods and will primarily be concerned with the Murphy and Riley methodology which involves the conversion of phosphate to 12-molybdophosphoric acid followed by the reduction thereof to a molybdenum blue complex. The Murphy and Riley method was first described in 1958 in the J. mar. biol. Ass. U. K. 37, 9–14. Initially the method called for the use of ascorbic acid as the reducing material. Shortly thereafter, in 1962 in Analytica Chim. Acta, 27, 31–36 Murphy and Riley described a modification of their method comprising the use of antimony to speed up the reaction.

A method of increasing the sensitivity of the Murphy and Riley analysis by adding a dye to the mixture was disclosed as early as 1966 by Itaya and Ui in Clinica Chimica Acta, 14, 361–6, then refined later by others including Van Veldhoven et al. in 1987 in Analytical Biochemistry, 161, 45–8. The presence of phosphomolybdic acid was found to shift the absorbance maximum of malachite green and other dyes and increase their molar absorptivities.

In the patent literature, International Application No. PCT/SE 93/00462 (WO 93/25900) to Kjell Persson, published 23 Dec. 1993, discloses and claims a multilayer reagent strip for the determination of phosphate in soil samples using essentially the Murphy and Riley methodology. The device comprises a layer of ascorbic acid affixed to a plastic strip overlaid with a layer of porous material impregnated with ammonium molybdate. In use the strip is immersed into a test tube containing hydrochloric acid and a soil sample, removed in two minutes and the resultant blue color compared to a color scale.

SUMMARY OF THE INVENTION

The present invention comprises a unitized test composition and device for determining inorganic phosphorus in various test samples. In combination with certain extraction procedures, the test composition and devices made therewith are accordingly well suited for the determination of phosphorus in field testing or on-site situations as well as in laboratories performing phosphorus testing procedures on large numbers of test samples. The composition comprises a molybdate salt such as ammonium molybdate which converts any phosphate present to 12-molybdophosphoric acid, a solid buffer system for maintaining the test sample and composition in a pH range of about from 0.3 to 3.0, and a chromogenic reducing material such as leuco Bindschedler's Green (LBG) for reducing the molybdophosphoric acid to molybdenum blue. It was found that LBG itself contributes to the total color formation of the test composition reaction thus increasing the sensitivity of the test composition. Preferably, the test composition is incorporated with a porous matrix such as absorbent filter paper so that the user can easily contact the test system with the fluid being tested for phosphorus content. The usual method for incorporating the composition with the porous matrix involves the impregnation of the matrix with a solution of the test reagent components followed by heat or vacuum drying which results in a dry reagent test device ideally adapted to field use.

DESCRIPTION OF THE PREFERRED EMBODIMENTS

As noted above, the present invention involves the use of a modified Murphy and Riley method for the determination of phosphorus or phosphates in test samples such as soil, ground water and biological materials. The advantages of this method are significant. The first is convenience. Most prior art test kits require more procedural steps and require significantly more time to reach a determination, mainly because they require the user to perform several steps using multiple liquid solutions. Secondly, advances in the chemical formulation used in the composition and devices of the present invention make the color display superior to that seen in the prior art. The use of a reducing dyestuff, such as Bindschedler's Green, leuco base, as the reductant in the formation of molybdenum blue and the heteropoly blues means that the byproduct of the reduction, Bindschedler's Green, contributes to the intensity of the developed color and increases the sensitivity of the test. Thirdly, the inclusion of a solid buffer as an integral part of the test composition offers a facile test system having significant advantages over the test systems and methodologies described in the literature and patent prior art.

The molybdate salts of the present composition and device can be any of the various aqueous soluble salts commercially available and compatible with the remaining constituents. Preferably, ammonium heptamolybdate tetrahydrate is the salt of choice but other salts such as sodium, potassium, calcium and lithium molybdate may also be utilized. The concentration of molybdate salt used in the formulation of the present invention range about from 1.0 to 20 g/L in the impregnating solution.

As noted above, in order to achieve the required sensitivity, a reducing dyestuff, preferably a leuco form, is substituted for the ascorbic acid reducing material described by Murphy and Riley. The leuco form 1 of the triphenylmethane and diphenylamine groups of reducing dyestuffs are preferable for use in the compositions of the present invention. Exemplary of the many reducing dyestuffs found to be useful are leuco Bindschedler's Green, leuco malachite green, leuco patent blue violet, leucoberbelin blue, leuco crystal violet, starch iodide and tetramethylbenzidine. Leuco Bindschedler's Green has been found to be especially useful in the present composition. The concentration of reducing dyestuff varies depending on the activity of the material selected; however, the usual range of concentration of dye in the impregnating solution varies about from 16 to 4000 mg/L.

As previously noted, the present composition, unlike prior art compositions and devices, includes a solid buffer for maintaining the test fluid and reagent composition in a pH range of about from 0.3 to 3.0. Solid buffer systems are ones which can be incorporated into a test reagent composition and perform the function of maintaining the test sample and reagent composition at a constant pH which is optimum for the calorimetric reaction to proceed. Exemplary of the solid state buffers which can be used in the present test system include the use of cyclamic acid, bromoacetic acid, lutidinic acid and o-nitrobenzoic acid. In the present invention, and when using a matrix to house the reagent composition, a cyclamic acid buffer system, which contributes to consistent color formation, has been found to constitute a significant improvement over prior art test systems. The rates and products of reactions producing color in these methods are well known to have strong dependencies on the acidity of the medium used.

The present formulation also utilizes a red background dye for the purpose of enhancing color distinctions as well as polyvinylpyrrolidone (PVP) for the purpose of muting interference that would otherwise be seen from silicates and other materials coextracted from the soil. PVP has been used in previous phosphate analysis schemes as a clarifier, color stabilizer, or catalyst. Selective elimination of silicate interference by PVP has not previously been demonstrated, however. Incorporation of from 8 to 78% dry weight PVP into a series of four test strip dip formulations similar to those described above showed an increasing tendency to eliminate the color attributed to the presence of added sodium metasilicate in standard phosphate samples.

The matrix of the present invention is used to house or contain the test compositions of the present invention. Usually this material is a flat absorbent paper or paper-like material which commonly is used as a filter material. Materials other than cellulosic paper such as membranes, sintered glass, glass fibers, flocculants, diatomaceous earth, activated carbon and so forth may also be used. Although the matrix is usually a flat material, other shapes such as cylindrical, oval and so forth may also be used depending on the specific application. As in most present day reagent strip products, for ease of handling and immersion into the fluid being tested, the paper matrix is usually attached to one end of a fluid impervious elongated strip of semirigid plastic material, using an attachment means such as double faced adhesive tape.

EXAMPLES

Example 1

Preparation of Test Strips

Test strips were prepared as follows. One liter of the "first dip" solution is prepared using the following procedure. First, prepare a submix by mixing 163.4 g. polyvinylpyrrolidone (PVP) K-60 (45% aqueous solution) with 200. g. purified water. Tap water was purified for these purposes by reverse osmosis followed by passage through a deionization column. Preparation of the second submix was begun by mixing 9.18 g. cyclamic acid, 6.10 g. sodium cyclamate, and 4.89 g. ammonium molybdate tetrahydrate with 618. g. purified water and mixing until all components were dissolved. Then, 0.03157 g. of the sodium salt of ponceau S was added to the second submix; the mix was stirred until homogeneous. Submix #1 was then added to submix #2 and mixed thoroughly to form dip #1. Filter paper (Whatman CCP500) was then dipped into dip #1, and the excess was scraped off from the surfaces. The paper was immediately dried for about five minutes at 250° F. (121° C.). This was accomplished through the use of an apparatus in which paper was dispensed from a roll, passed through a dip pan containing dip #1, passed through a drier utilizing gas and infrared heaters with forced air circulation, and collected on a takeup roll.

A solution labeled dip #2 was prepared by mixing 0.249 g. Bindschedler's Green, leuco base, with 1.0 L of reagent alcohol and stirring until homogeneous. Dry paper with dip #1 applied was then passed through dip #2 and dried for about 3.3 minutes at 200° F. (93° C.), then collected on a takeup reel. Double-sided tape (3M #415) was applied to one side of the paper as it emerged from the drier. By means of automated mechanical cutting equipment, test strips having 0.4"×0.5" paper pads fixed to 3.25"×0.5" transparent plastic supports were prepared. The test strips were stored with silica gel desiccant packets in plastic bottles until the time of use.

Example 2

Use of the Test Strips

The procedure for determining phosphate as phosphorus in a soil sample is simple. Soil is measured by volume; 1.7 cc. of soil is mixed with 11.7 mL of extractant in a plastic vial and shaken for one minute. The extractant is an aqueous solution with 40 mM sodium bisulfate, 30 mM sodium fluoride, and 0.20M sodium chloride. A test strip is dipped into the extractant solution for ten seconds, then removed and held level for one minute. The color read through the transparent support is then compared with a printed color chart showing colors (termed color blocks) for 1, 4, 10, and 25 ppm phosphorus. Because of the dilution of soil phosphate into the extractant, these correspond to 6, 23, 59, and 146 ppm phosphorus in the soil sample, a range appropriate for making a determination about whether to add a phosphate-containing fertilizer to a vegetable or flower garden.

The accuracy of phosphate determination achieved by the present invention was verified by analysis of 24 soils of widely varied origin and comparison of test strip results with Bray method results supplied by an independent laboratory. Soil test strips were compared with either a prepared color chart or test strips dipped into standard solutions, and readers found in several studies that 87–96% of the soils had phosphate levels determined correctly within one color block and 75–88% of the soils had phosphate levels determined correctly within one half of one color block of the true value as determined by independent Bray analysis.

What is claimed is:

1. A test device for the determination of inorganic phosphorus in aqueous test samples comprising a porous absorbent matrix incorporated with the dry residue of a reagent composition comprising:
   A. an effective amount of a molybdate salt capable of reacting with any inorganic phosphorus present in the aqueous test sample to form 12-molybdophosphoric acid;
   B. a solid buffer system capable of maintaining the test composition in a pH range of about from 0.3 to 3.0 when the matrix is contacted with the aqueous test sample; and,
   C. an effective amount of a chromogenic material capable of reducing the 12-molybdophosphoric acid to a molybdenum blue complex, the oxidized chromogenic material and the molybdenum blue together forming a complex chromophoric product in an amount proportional to the amount of phosphorus in the aqueous test sample.

2. A test device as in claim 1 wherein the chromogenic reducing material is the leuco form of a material selected from the group consisting of triphenylmethane and diphenylamine dyes.

3. A test device as in claim 1 wherein the chromogenic reducing material is selected from the group consisting of leuco Bindschedler's Green, leuco malachite green, leuco patent blue violet, leucoberbelin blue, leuco crystal violet, starch iodide and tetramethylbenzidine.

4. A test device as in claim 1 wherein the chromogenic reducing material is leuco Bindschedler's Green.

5. A test device as in claim 1 wherein the buffer system comprises cyclamic acid and a cyclamate salt.

6. A test device as in claim 1 wherein the test composition is maintained at a pH of about 2.0.

7. A test device as in claim 1 wherein the molybdate salt is selected from the group consisting of ammonium, sodium, potassium, calcium, magnesium and lithium molybdates.

8. A test device as in claim 7 wherein the molybdate salt is ammonium heptamolybdate tetrahydrate.

9. A test device as in claim 1 wherein the porous absorbent matrix is a material selected from the group consisting of natural and synthetic paper and polymeric membranes.

10. A test device as in claim 1 wherein the porous absorbent matrix is cellulosic paper.

11. A method for the determination of inorganic phosphorus in aqueous test samples, said method comprising:
   A. Contacting the test sample with a test reagent composition comprising a molybdate salt, a solid buffer for maintaining the mixture of test sample and reagent composition in a pH range of about from 0.3 to 3.0, and a chromogenic reducing material to produce a colored reaction product consisting of molybdenum blue and the oxidized form of the chromogenic reducing material;
   B. Measuring the amount of color produced by the reaction of the test reagent composition with the phosphorous in the test sample; and,
   C. Converting the measured amount of color produced to concentration of inorganic phosphorus in the test sample.

12. A method as in claim 11 wherein the chromogenic reducing material is selected from the group consisting of the leuco form of triphenylmethane and diphenylamine dyes.

13. A method as in claim 11 wherein a solution of the test reagent composition is incorporated with a matrix material and dried.

14. A method as in claim 13 wherein the matrix is absorbent paper.

15. A method as in claim 11 wherein the buffer comprises a cyclamate salt and cyclamic acid.

16. A method as in claim 11 wherein the chromogenic reducing material is leuco Bindschedler's Green.

17. A method as in claim 11 wherein the molybdate salt is ammonium heptamolybdate tetrahydrate.

18. A method as in claim 11 wherein the aqueous test sample comprises a solution of phosphorus from soil prepared from an aqueous extracting solution of bisulfite, fluoride and chloride salts.

* * * * *